United States Patent [19]

Hare et al.

[11] Patent Number: 5,554,028
[45] Date of Patent: Sep. 10, 1996

[54] DENTAL IMPRESSION TAKING

[75] Inventors: Robert V. Hare, Georgetown, Del.; Paul D. Hammesfahr, Stuart, Fla.

[73] Assignee: Dentsply Research & Development Corp., Milford, Del.

[21] Appl. No.: 217,527

[22] Filed: Mar. 24, 1994

[51] Int. Cl.$^6$ ........................................ A61C 9/00
[52] U.S. Cl. .......................................... 433/214
[58] Field of Search ............................... 433/214

[56] References Cited

U.S. PATENT DOCUMENTS

| | | | |
|---|---|---|---|
| 4,198,243 | 4/1980 | Tanaka | 106/19 |
| 4,431,631 | 2/1984 | Clipper et al. | 424/53 |
| 4,537,778 | 8/1985 | Clipper et al. | 424/53 |
| 4,839,156 | 6/1989 | Ng et al. . | |
| 5,116,222 | 5/1992 | Futami et al. | 433/48 |

FOREIGN PATENT DOCUMENTS

| | | | |
|---|---|---|---|
| 2170406 | 8/1986 | United Kingdom . | |
| WO93/04664 | 3/1993 | WIPO | A61K 7/20 |

OTHER PUBLICATIONS

Database WPI, Week 97, Derwent Publications Ltd., London, GB; AN 95133356.
Dent Mater 9:209–213, May, 1993, "Implications of the presence of dithiocarbamate in latex gloves", B. E. Causton, F. J. T. Burke, N. H. F. Wilson.
Fundamentals of Fixed Prosthodontics, ed 2, Chicago Quisatessence Publishing Co., pp. 201–219, 1981—Shillingburg/Hobo/Whitsett.
Dental Products Report, Dec. 89, 3 pages Testing the Effects of Latex Gloves and Tissue Management Compounds on the Setting Process of Addition–Silicone Impression Materials.
Pre'–emp Pre–Impression Mouthwash, 3 pages, Jan. 1989.
The antimicrobial activity of Prevention mouthrinse, American Journal of Dentistry vol. 6, No. 5, Oct., 1993—4 pages.

*Primary Examiner*—Nicholas D. Lucchesi
*Attorney, Agent, or Firm*—Edward J. Hanson, Jr.; James B. Bieber; Douglas J. Hura

[57] ABSTRACT

A method of preparing an impression of dentition in the oral cavity is provided that overcomes a problem of transfer of inhibitors left by latex gloves that interfere with platinum catalyzed hydrosilation reactions. The method involves applying a surfactant, preferably with peroxide, to the area that is to have its impression taken substantially immediately before applying the impression taking material, rinsing the composition from the area and proceeding with the taking of the dental impression. Preferably the decontaminating composition consists essentially of surfactant, especially polyoxyethylene surfactants, hydrogen peroxide and water.

9 Claims, 2 Drawing Sheets

DENTAL IMPRESSION TAKING

BACKGROUND OF THE INVENTION

This invention relates to methods of effectively making dental impressions and compositions to prepare the dentition for the taking of dental impressions.

For a number of years protective gloves have been worn by all personnel in dental operatories when hands will contact dental patients as an asepsis protection or shield to or against patient to patient or patient to operatory personnel transfer of disease or toxins. During this period of time there has been a well reported problem with materials in and on latex gloves inhibiting the surface cure of vinyl polysiloxane dental impression materials. The surface cure of the dental impression is critical to an exact detailed production of the dental prosthetic utilizing the dental impression. The materials suspected of being transferred from the gloves are materials such as the sulfur containing compounds that are residues of the manufacturing process of latex gloves, see Dent Mater 9:209–213, May, 1993, "Implications of the presence of dithiocarbamate in latex gloves", B. E. Causton[1], F. J. T. Burke[2], N. H. F. Wilson[2] the contents of which are incorporated herein by reference. These materials are present to varying degrees. Surface inhibition causes a loss of detail at the interface between the impression material and the dentition. The problem appears to occur when the surface of a glove or even an instrument or object such as a cotton swab or retraction cord that was handled by a gloved hand, has any of the inhibiting substance on it and then contacts the dentition. This seems to result in the transfer of the inhibiting substance to dentition surfaces that are subsequently contacted by the dental impression material. This has been observed to inhibit the optimal cure of the impression material at the interface. This results in a loss of detail at the very place where detail is generally most important and critical. The production of good and aesthetically pleasing dental facings, crowns and other prosthetic parts as well as their fit and superior efficacy is affected by the quality of detail in the dental impression.

It has been the general practice to clean the area of dentition that is to have its impression taken with water rinsing and drying with air. Flour of pumice is also used in some instances. This cleaning has been employed to remove blood, saliva, ground tooth structure and other debris. It has been unknown to employ a method to effectively decontaminate dentition from glove imparted vinyl polysiloxane cure inhibition. This inhibition, in part at least, is believed to be due to the fact that the impression material is platinum catalyzed and is from imperical observation inhibited by those interfering substances in or associated with latex gloves. Further, it is common to add surfactants to vinyl polysiloxane products in order to reduce their inherent hydrophobic nature, rendering them somewhat hydrophilic, and thus it is believed adding to the problem by "pulling in" the contaminating inhibiting material.

Hydrogen peroxide has been used as an antiseptic in the mouth for many years. During routine oral examination and cleaning, the scaling of the teeth may disturb the gingival soft tissue. There may be bleeding and numerous bacteria that are released into the mouth. The hygienist will often instruct the patient to rinse their mouth with a one to one aqueous dilution of dilute hydrogen peroxide for several days after the visit. This is to help the tissue heal faster.

In a procedure to produce a Dicor® MGC Inlay (Dicor is a trademark of Dentsply International, Inc.), one of the steps is to coat the prepared tooth with a surfactant to allow the imaging powder to coat the surface. The Dicor MGC Imaging liquid consists of 30% Tween 20 (Polysorbate 20), the remainder being water. This solution is painted on the prepared tooth, blown to a thin film and then coated with powder. This product was introduced in February 1990 and has been used in the mouth for almost four years with virtually no complaints.

An object of the invention is to provide a method of producing a superior dental impression.

A further object is to provide a decontaminating composition that will prepare dentition for receipt of dental impression material providing for the taking of a superior dental impression.

An object of the invention is to minimize the necessity of making remakes of the dental impressions.

Other objects and advantages of the present invention will become apparent from the following detailed description when viewed in conjunction with the accompanying drawings, which set forth certain embodiments of the invention.

SUMMARY OF THE INVENTION

By the present invention in one aspect, a method of preparing an impression of dentition in the oral cavity is provided. The method involves sequentially applying a composition comprising a surfactant to an area that is to have its impression taken substantially immediately before applying the impression taking material to the area, rinsing the composition from the area that is to have its impression taken, applying an impression taking material to the area and forming the impression material into intimate contact with the area that is to have its impression taken and setting the impression material in the impression of the area. Preferably the composition includes hydrogen peroxide. The invention is particularly concerned with impression materials set by platinum catalyzed hydrosilation reactions. By another aspect of the invention a dental composition is provided that consists essentially of a carrier, peroxide and a surfactant. The preferred carrier is water present in an amount of 90 to 97.5%. The preferred peroxide is hydrogen peroxide present in an amount of about 2 to 4% and the preferred surfactant is polyoxyethylene present in an amount of about 0.5 to 5%.

DESCRIPTION OF THE PREFERRED EMBODIMENTS

Figure 1:
FIG. 1 is a photomicrograph of a dental impression of an uncontaminated prepared tooth surface.

The essential ingredients of the preferred composition of the present invention are peroxides and surfactants. The preferred peroxide is hydrogen peroxide. Preferably water is also present and functions as a carrier and diluent. Preferably the composition is a free flowing liquid having a viscosity at least not much greater than water.

Peroxides useful in the current invention include hydrogen peroxide and organic peroxides such as benzoyl peroxide, carbamyl peroxide, tert-butyl peroxide, lauryl peroxide and diisononayl peroxide and mixtures of such peroxides. In the most preferred composition of the present invention the peroxides are chosen to avoid toxicity and minimize stinging and burning especially on sensitized mucosa that has been damaged in operatory procedures during preparation of the tooth substance. It is also desirable to minimize any unpleasant taste or smell involved in the use of the compositions. The peroxides and especially the preferred hydrogen peroxide is preferably present in an amount of 0.5 to 10% more preferably 1 to 5% and most preferably 2 to 4%. Hydrogen peroxides suitable for use in the present invention are those typically known for use in the oral cavity.

Suitable carriers and diluents would preferably include water and mono alcohols such as methyl, ethyl and propyl alcohol or mixtures thereof. The monohydric alcohols are considered to be carriers and may also function as homogenizing and solubilizing aspects. In the most preferred compositions of the present invention, the carriers and diluents are selected to avoid toxicity and preferably cause no unpleasant taste, smell, stinging or burning in the composition. In the most preferred compositions the only carrier-diluent is water. Preferably the carrier-diluent is present in an amount of 50–99%, more preferably 75–98% and most preferably 90 –97.5%.

Preferably the surfactant is present in the preferred compositions of the present invention in an amount of 0.1 to 40% more preferably 0.25 to 20% and most preferably 0.5 to 5%. A wide breadth of surfactants are suitable for use in the present invention. Surfactants should be chosen for their lack of toxicity and freedom from taste and smell or for a pleasant taste and/or smell. The surfactants preferably do not yield a stinging or burning sensation in use. The effervescence caused by the foaming of the peroxide may enhance any tendency to toxicity, taste, smell, stinging or a burning sensation.

The ingredients of the composition of the present invention are preferably compatible in use and preferably during storage as homogeneous solutions at usual ambient temperature 21° C. and conditions found in dental operatories, preferably without refrigeration for at least 6 months or more preferably at least one year or longer. In particular, in choosing the surfactant, it is desirable to find a preferred surfactant which in combination will provide all of the aforesaid properties in a solution of hydrogen peroxide and a water carrier-diluent.

The surfactant may be selected from the group consisting of the classes of surfactants that include nonionic, anionic and cationic surfactants and mixtures thereof. Nonionic surfactants are preferred and more preferred are the polyoxyethylene based surfactants.

Flavoring agents, coloring and pigmenting agents hemostatic and/or astringents and stabilizer and the like may be included but are considered non essential, non functional ingredients to the present invention. In the most preferred embodiments flavoring agents, coloring and pigmenting agents, hemostatic and/or astringents and the like are preferably not included because they are considered unnecessary with the proper selection of the hydrogen peroxide, surfactant and in more preferred embodiments the diluent carrying agents. Unnecessary agents at best generally add expense and often leave residues which interfere with obtaining the best impression.

Gelling agents may be desirable in some instances and are considered functional ingredients to the present invention because they change the way the treatment is carried out. The preferred compositions of the present invention are very fluid, as this aids in a superior contact of the surface to be decontaminated and also in the removal of the decontaminating composition or compositions. The foaming of the hydrogen peroxide aids in providing in-situ active decontamination and removal of the residues, the removal of which are desired. Other functional ingredients would be polyhydric alcohols used for viscosity modifying.

In a typical procedure to carry out the method of the invention in performing a dental restoration, a dental clinician would make a dental preparation, for example, a crown preparation. Typically in preparing a crown restoration a tooth would have its exposed bulk reduced from all dimensions to a stump upon which a crown would be mounted. Generally the next procedure would be a rinsing away of any debris and fluids with water.

This would be followed typically by a method of preparing an impression of dentition in situ in the oral cavity (mouth) of a patient. The clinician would in the preferred procedure perform a decontaminating treatment using the compositions of the present invention. The decontaminating surfactant, and more preferably the preferred composition of the present invention, is applied to the area that is to have its impression taken. This should preferably be done substantially immediately before applying the impression taking material to the area. Preferably the decontamination composition is applied with a swab with light rubbing to assure good contact without damaging the soft tissue of the mucosa. A cotton swab is preferred because of its good properties and ready availability. The decontaminating composition is preferably left in contact with the dentition for from 10 to 360 seconds, more preferably 15 to 60 seconds and most preferably 20 to 40 seconds. The decontaminating composition is then removed, preferably washed away, by rinsing with water and removal from the mouth, typically with an aspirator. Next the dentition is air dried, typically with regular office air that is preferably free of ingredients such as lubricants.

Next the dental clinician would prepare to take a high resolution dental impression, and in the primary use of the present invention, use a vinyl siloxane that is platinum catalyzed. The dental impression material is applied to the area that is to have its impression taken in conventional manner. The dental impression material is formed into intimate contact with the area. The dental impression material is set; in the case of self curing dental impression materials, this means the dental impression material is left in place long enough to set in the impression of the area. After the dental impression material is set, the dental impression is removed from the oral cavity (mouth) and inspected visually for accuracy of detail. Methods of making clinical dental impression are well known, for example, many are represented in the text *Fundamentals of Fixed Prosthodontics*, ed 2. Chicago Quisatessence Publishing Co. pp 201–219, 1981. Shillingburg Jr HT, Haba S, Whitsett LD: the contents of which are incorporated herein by reference.

In this patent application all percents (%) are weight percents based upon 100% in the total final composition.

The invention is further illustrated by the following examples.

EXAMPLE 1

A solution of the following ingredients was prepared by charging the 3% hydrogen peroxide solution into a glass flask and adding the surfactant via a funnel by pouring. After addition the flask was shaken to achieve a uniform solution.

| INGREDIENTS | CAS. NO. | PERCENT |
|---|---|---|
| 3% Hydrogen Peroxide in water solution USP | 7722-84-1 | 98.0 |
| polyoxyethylene (20) sorbitan monolaurate Tween 20 NF (Polysorbate 20) from ICI Americas Inc. | 9005-64-5 | 2.0 |
| Total | | 100.0 |

To demonstrate the effectiveness of the solution in example 1), a bovine incisor was sanded flat with 600 grit wet sandpaper. This surface was sanded until an area of dentine was exposed in the center of the sanded surface. (Shown in FIG. 4) Note: the crack in the tooth surface is an artifact caused by pulling high vacuum on the specimen in the S.E.M. (Scanning Electron Microscope).

Figure 4:
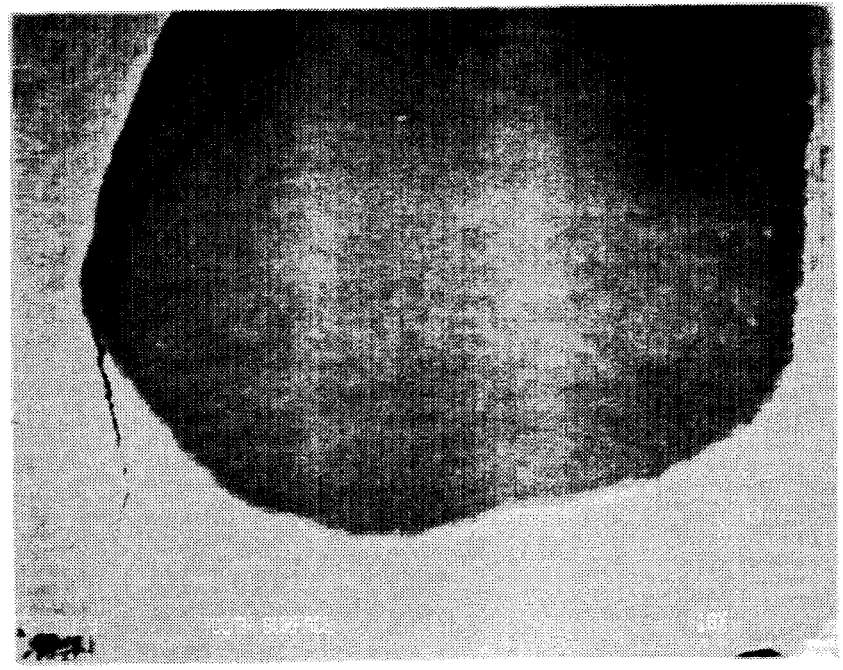
FIG. 4 is a photomicrograph of the tooth surface taken by the impressions of FIGS. 1, 2 and 3.

FIG. 1 is an S.E.M. of the impression surface of the same tooth shown in FIG. 4. This shows the impression of a uncontaminated surface of the bovine incisor described above.

Figure 2:
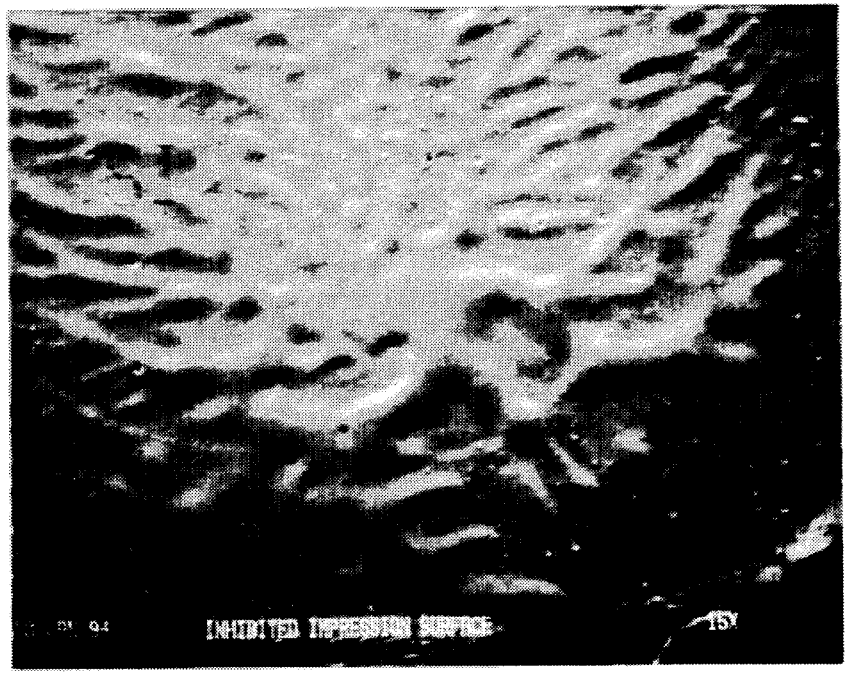
FIG. 2 is a photomicrograph of a dental impression of the same prepared tooth surface contaminated.

FIG. 2 is an S.E.M. of the impression of the same tooth contaminated by rubbing the surface of the tooth with a latex glove, Conform, a product of Ansell Edmont. The surface detail of the impression is lost due to the inhibition of the cure.

Figure 3:
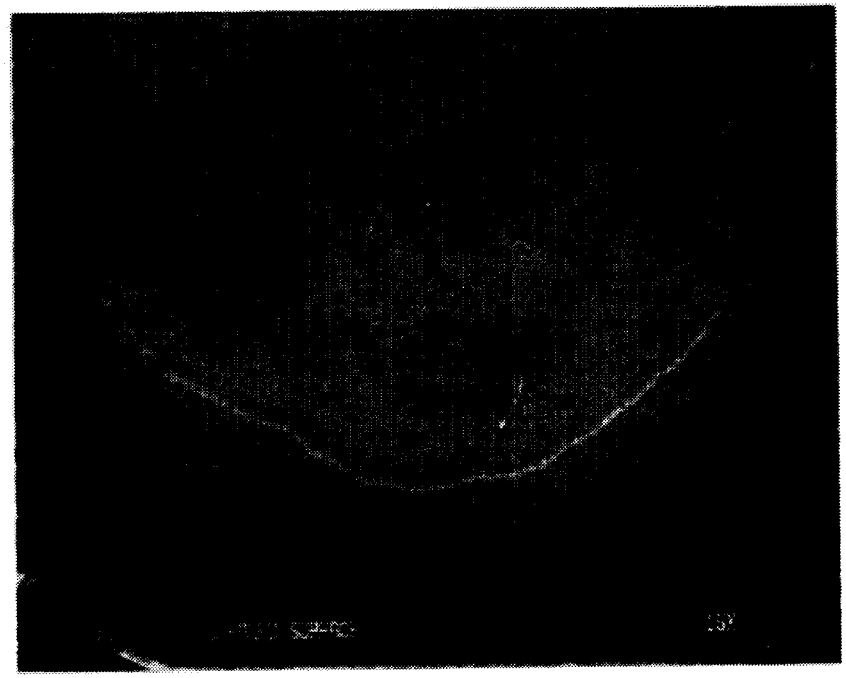
FIG. 3 is a photomicrograph of a dental impression of the same contaminated prepared tooth surface shown in FIG. 2 but treated according to the present invention prior to taking the impression.

FIG. 3 is an S.E.M. of the impression of the same tooth contaminated with a latex glove as in FIG. 2 and then cleaned with the solution in Example 1. The surface of the tooth was swabbed with a cotton pellet saturated with the solution described above for 30 sec., then rinsed with water for 20 sec. and air dried. The impression of the surface was then made. The detail of the impression in FIG. 3 is as good as the detail in FIG. 1 showing the effectiveness of the solution in Example 1.

FIG. 4 is an S.E.M. of the bovine incisor itself.

All of the specimens were prepared for S.E.M. by coating with Ag/Pd by evaporative deposition and then viewing and photographing at the following S.E.M. separating conditions. Voltage=10 KV, magnification=15X, tilt angle=30°, secondary electron detector.

EXAMPLES 2–12

The solutions set forth in the following table were prepared substantially as set forth in Example 1. The ingredients were added in order, from the ingredient of the greatest volume to the ingredient of the least volume.

| | EXAMPLE | | | | | | | | | | |
|---|---|---|---|---|---|---|---|---|---|---|---|
| INGREDIENTS | 2 | 3 | 4 | 5 | 6 | 7 | 8 | 9 | 10 | 11 | 12 |
| Deionized Water | 100 | 0 | 0 | 98 | 0 | 0 | 0 | 98 | 0 | 0 | 0 |
| 190 proof Ethanol USP | 0 | 100 | 0 | 0 | 98 | 0 | 15 | 0 | 98 | 15 | 0 |
| 3% Hydrogen Peroxide in water solution USP | 0 | 0 | 100 | 0 | 0 | 98 | 83 | 0 | 0 | 83 | 98 |
| Polysorbate 20 (Tween 20) | 0 | 0 | 0 | 0 | 0 | 0 | 0 | 2 | 2 | 2 | 2 |
| Hül's P5071 Dimethyl Siloxane Ethylene Oxide Copolymer | 0 | 0 | 0 | 2 | 2 | 2 | 2 | 0 | 0 | 0 | 0 |
| Homogeneous Solution? | Yes | Yes | Yes | No | No | Yes | No* | Yes | Yes | Yes | Yes |
| Results Inhibition of set. | SB | SB | SL | SL | SL | SL | G | SL | SL | G | G |

All entries in Table are weight % based upon 100% of final composition
ALL RESULTS ARE BASED ON UNAIDED EYE VISUAL OBSERVATION
*clear solution at first
SB = Substantial inhibition
SL = Slight inhibition, somewhat effective
G = Good results - no inhibition

TEST PROCEDURE

Eleven extracted human tooth were contaminated by hand rubbing with a latex glove for 15 to 30 seconds over the tooth's surface. The glove was a Healthco glove as identified in the previously referenced article "Implications of the presence of dithiocarbamate in latex gloves". An impression of the contaminated tooth was made using a vinyl siloxane light body Reprosil® (product of the L.D. Caulk Co. Division of Dentsply International Inc.) dispensed from a preloaded impression material carriage and allowed to flow onto the tooth's surface. The dental impression material remained in place for 15 minutes in situ as applied. The cured dental impression was peeled back from the tooth surface and the tooth and dental impression were visually inspected with the unaided eye. All eleven teeth were found to have uncured impression material on their surface. All eleven teeth were then cleaned by wiping clean with a piece of cheese cloth.

The eleven teeth were then recontaminated with the latex glove and then each was treated according to a different respective Example 2–12 by lightly rubbing with the respective composition of the respective Example using a cotton swab. One tooth was used for each example. After treatment each tooth was rinsed with water applied from a lab squeeze bottle for 30 seconds after which the tooth was dried with gentle application of dry compressed air from a 25 psi tank. Thereafter the vinyl siloxane impression material described above was applied to each tooth as described above and the results are given below:

From the test it was concluded that:

Example 11 and 12 gave the best performance with peroxide and Tween surfactant.

Example 8 yielded the next best result using peroxide and a surfactant that alcohol was used with to achieve solution in the peroxide (water) solution. Phase separation, however, occurred after 3 days.

Example 9 was next in preference using water and Tween. The solution was fairly effective and the solution stable.

Example 10 with alcohol and surfactant worked about as well as water and surfactant, but could result in a burning sensation in use.

Example 4 using peroxide alone was not as effective as the above experiments.

Examples 2 and 3 respectively of water alone and Ethanol alone were not effective.

Example 5, a solution was not obtained. Water and silicone surfactant proved to be immiscible.

Example 6, alcohol same as Example 7 peroxide and silicon surfactants.

Example 5 immiscible.

EXAMPLE 13

A procedure for evaluating pre-treatment solutions that does not require the use of an extracted human or bovine tooth was developed.

Materials needed to do the test
1) Latex gloves. (Known to cause inhibition of VPS impression materials.
2) Parchment mix pad.
3) Vinyl polysiloxane impression addition cured platinum catalyzed material; syringe or regular viscosity.
4) Tweezers and cotton pellet or swab.
5) Pre-treatment solution.

Procedure
A.) Rub a latex glove onto the surface of the parchment pad. Rub vigorously over a large area for at least 30 seconds with moderate pressure.
B.) Using the tweezers pick up a cotton pellet saturated with pre-treatment solution and scrub one half of the latex contaminated surface for 30 seconds.
C.) Rinse the parchment with water for 10 seconds, then blow dry with air.
D.) Mix the impression material according to package instructions and apply it over the pre-treated and non-treated surface of the parchment pad; allow to completely cure (15 minutes at 23° C.).
E.) Peel up the impression and examine the parchment for inhibited material. Inhibition of set will be noted to the naked eye as having a wet appearance on the VPS and the parchment. Rubbing the VPS material in the area corresponding to the untreated side of the parchment pad using a cotton swab results in material transfer to the cotton swab. Rubbing the treated side will not result in transfer of material to the cotton swab with pretreatment solutions represented by this invention.

The present invention provides for neutralizing the effects of inhibitors, especially those left on dentition by rubber gloves during preparation for taking a dental impression using platinum catalyzed hydrosilation reactions to set the dental impression material. The method of decontaminating the dentition just before the impression material is applied assures high success in obtaining good impressions and thereby making superior dental prosthetics for the dental patient.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

It is claimed:

1. A method of preparing an impression of dentition in the oral cavity comprising the steps of sequentially applying a composition comprising a surfactant to an area that is to have its impression taken substantially immediately before applying the impression taking material to said area, rinsing said composition from said area that is to have its impression taken, applying an impression taking material to said area and forming said impression material into intimate contact with said area that is to have its impression taken, and setting said impression material in the impression of said area.

2. The method of claim 1 wherein said composition comprises peroxide.

3. The method of claim 2 wherein said surfactant is a nonionic surfactant.

4. The method of claim 2 wherein said peroxide is present in an amount of about 0.5–10% by weight of the total composition.

5. The method of claim 2 wherein the peroxide is hydrogen peroxide and the surfactant is present in an amount of about 0.25–20% by weight of the total composition.

6. The method of claim 1 wherein said impression material is set by platinum catalyzed hydrosilation reactions.

7. The method of claim 1 wherein said composition comprises water.

8. The method of claim 7 wherein said water is present in an amount of about 75–98% by weight of the total composition.

9. The method of claim 1 wherein said surfactant is a polyoxyethylene.

* * * * *